United States Patent
Jain et al.

(10) Patent No.: US 8,017,405 B2
(45) Date of Patent: Sep. 13, 2011

(54) GAS ANALYSIS METHOD

(75) Inventors: Ravi Jain, Bridgewater, NJ (US); YuDong Chen, Bridgewater, NJ (US)

(73) Assignee: The BOC Group, Inc., Murray Hill, NJ (US)

(*) Notice: Subject to any disclaimer, the term of this patent is extended or adjusted under 35 U.S.C. 154(b) by 1262 days.

(21) Appl. No.: 11/500,131

(22) Filed: Aug. 7, 2006

(65) Prior Publication Data

US 2007/0031974 A1   Feb. 8, 2007

Related U.S. Application Data

(60) Provisional application No. 60/706,330, filed on Aug. 8, 2005.

(51) Int. Cl.
  *G01N 33/00*  (2006.01)
(52) U.S. Cl. ........ 436/133; 436/119; 436/120; 436/161; 422/88; 73/23.2
(58) Field of Classification Search .............. 436/8, 133, 436/119, 120, 121, 161; 422/69, 88; 73/23.2
See application file for complete search history.

(56) References Cited

U.S. PATENT DOCUMENTS

| | | | |
|---|---|---|---|
| 2,594,268 A | 4/1952 | Geisel | |
| 4,332,781 A | 6/1982 | Lieder et al. | |
| 5,512,260 A | 4/1996 | Kiliany et al. | |
| 5,536,301 A | 7/1996 | Lansbarkis et al. | |
| 5,674,463 A | 10/1997 | Dao et al. | |
| 5,704,965 A | 1/1998 | Tom et al. | |
| 5,858,068 A | 1/1999 | Lansbarkis et al. | |
| 6,099,619 A | 8/2000 | Lansbarkis et al. | |
| 6,165,251 A | 12/2000 | Lemieux et al. | |
| 6,402,813 B2 | 6/2002 | Monereau et al. | |
| 6,441,264 B1 | 8/2002 | LeMaire et al. | |
| 6,511,528 B1 | 1/2003 | Lansbarkis et al. | |
| 6,797,036 B2 | 9/2004 | Funke et al. | |
| 6,962,629 B2 | 11/2005 | Johnson | |
| 7,135,604 B2 | 11/2006 | Ding | |
| 2002/0150522 A1 | 10/2002 | Heim et al. | |
| 2003/0197852 A1 | 10/2003 | Johnson et al. | |
| 2003/0198585 A1 | 10/2003 | Salma et al. | |
| 2003/0200866 A1 | 10/2003 | Weyrich et al. | |
| 2004/0052708 A1 | 3/2004 | Rao et al. | |
| 2005/0019240 A1 | 1/2005 | Lu et al. | |
| 2005/0098495 A1 | 5/2005 | Hughes | |
| 2005/0265912 A1 | 12/2005 | Alvarez, Jr. et al. | |
| 2007/0028764 A1 | 2/2007 | Wittrup et al. | |
| 2007/0028766 A1 | 2/2007 | Jain | |

(Continued)

FOREIGN PATENT DOCUMENTS

WO   WO 03/006374 A1   1/2003

(Continued)

OTHER PUBLICATIONS

European Search Report, Sep. 3, 2009.

*Primary Examiner* — Lyle Alexander
(74) *Attorney, Agent, or Firm* — Joshua L. Cohen

(57) ABSTRACT

The present invention provides a method for analyzing gases such as carbon dioxide, and includes passing a gas stream containing impurities into a gas adsorption means for a length of time at ambient or higher temperatures to adsorb the impurities therein, stopping the flow of the gas stream, and desorbing and analyzing the impurities using a detector.

14 Claims, 1 Drawing Sheet

U.S. PATENT DOCUMENTS

| | | |
|---|---|---|
| 2007/0028772 A1 | 2/2007 | Jain et al. |
| 2007/0028773 A1 | 2/2007 | Jain et al. |
| 2007/0031302 A1 | 2/2007 | Wittrup et al. |
| 2007/0031309 A1 | 2/2007 | Jain et al. |

FOREIGN PATENT DOCUMENTS

| | | |
|---|---|---|
| WO | WO 2004/077015 A2 | 9/2004 |

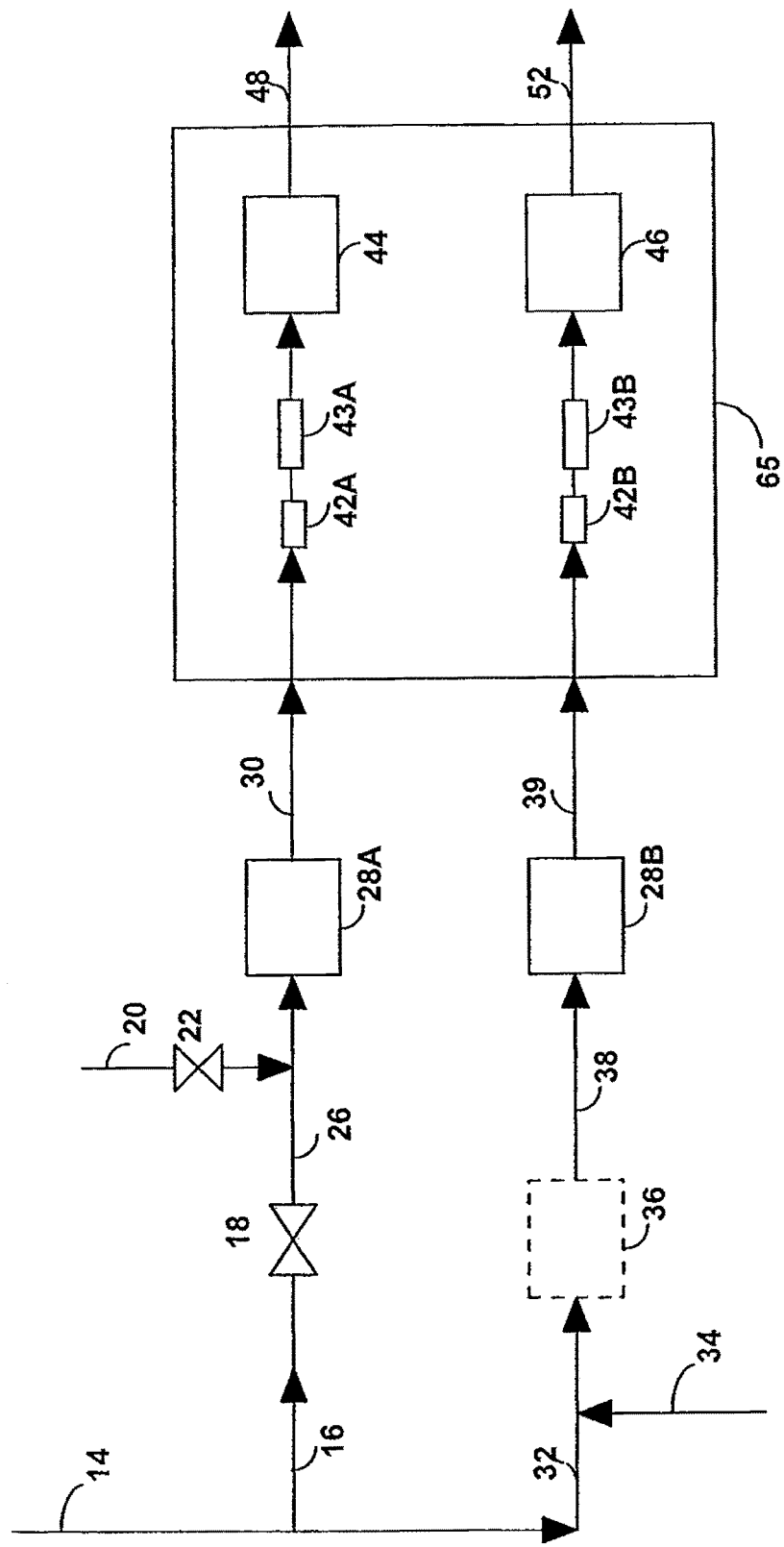

GAS ANALYSIS METHOD

FIELD OF THE INVENTION

The present invention provides a method of analyzing gases. More particularly, this invention provides a method of analyzing the amount of impurities in carbon dioxide during the production and/or purification process.

BACKGROUND OF THE INVENTION

Carbon dioxide is used in a number of industrial and domestic applications, many of which require the carbon dioxide to be free from various impurities. Unfortunately, carbon dioxide obtained from natural sources such as gas wells, chemical processes, fermentation processes or produced in industry, particularly carbon dioxide produced by the combustion of hydrocarbon products, often contains impurity levels of sulfur compounds such as carbonyl sulfide (COS) and hydrogen sulfide ($H_2S$), oxygenates such as acetaldehydes and alcohols, and aromatics such as benzene. When the carbon dioxide is intended for use in an application that requires the carbon dioxide to be of high purity, such as in the manufacture and cleaning of foodstuffs and beverage carbonation, medical products and electronic devices, the sulfur compounds and other hydrocarbon impurities contained in the gas stream must be removed to very low levels prior to use. The level of impurity removal required varies according to the application of carbon dioxide. For example, for beverage application the total sulfur level in carbon dioxide ($CO_2$) ideally should be below 0.1 ppm and aromatic hydrocarbons need to be below 0.02 ppm. For electronic cleaning applications removal of heavy hydrocarbons to below 0.1 ppm is required.

In order to ensure that the purification methods are removing impurities to the required levels analysis methods to measure impurities such as sulfur compounds, aldehydes, alcohols and aromatics reliably and cost-effectively at very low (ppm and ppb) levels are needed. Various methods for the analysis of these impurities are available and include gas chromatographs with various detectors, total hydrocarbon and total sulfur analyzers, GC/MS and some infrared based detectors. Most of the available analysis methods cost tens of thousands of dollars and are cost prohibitive for many carbon dioxide production and purification plants.

The present invention provides a simple, efficient and lower cost analysis method for various impurities in gases such as carbon dioxide during production, purification and usage.

SUMMARY OF THE INVENTION

The present invention provides a method for measuring the concentration of impurities during the purification of a gas comprising: a) passing a gas stream containing impurities into a gas adsorption means for a length of time at ambient or higher temperatures to adsorb the impurities therein; b) stopping the flow of the gas stream; and c) desorbing and analyzing the resulting gas stream using a detector.

The present invention also provides for an analytical method for measuring the concentration of impurities during the production and purification of carbon dioxide comprising: a) passing a gas stream containing impurities into a gas adsorption means for a length of time at ambient or higher temperatures to adsorb the impurities therein; b) stopping the flow of the gas stream; and c) desorbing and analyzing the resulting gas stream using a detector.

In an embodiment, the gas stream is a carbon dioxide gas stream. The gas adsorption means is a packed adsorption bed in a chromatograph. The chromatograph is a gas chromatograph. The detector may be a flame ionization detector (FID) and photometric ionization detector (PID) to detect hydrocarbon impurities and a detector such as flame photometric detector (FPD), sulfur chemiluminiscence detector (SCD) and pulsed flame photometric detector (PFPD) to detect sulfur related compounds.

BRIEF DESCRIPTION OF THE DRAWINGS

While the specification concludes with claims distinctly pointing the subject matter that Applicants regard as their invention, the invention would be better understood when taken in connection with the accompanying sole drawing in which the FIGURE is a detailed description of the analytical skid.

DETAILED DESCRIPTION OF THE INVENTION

The carbon dioxide that is typically produced for industrial operations has a number of impurities present in it. These impurities will often be a concern for many uses of the carbon dioxide, but in the production of products intended for human consumption such as carbonated beverages, and electronic manufacturing the purity of the carbon dioxide is paramount and can influence the taste, quality, and legal compliance of the finished product.

The impure carbon dioxide which can be obtained from any available source of carbon dioxide will typically contain as impurities sulfur compounds such as carbonyl sulfide, hydrogen sulfide, dimethyl sulfide, sulfur dioxide and mercaptans, hydrocarbon impurities such as aldehydes, alcohols, aromatics, propane, ethylene, and other impurities such as water, and carbon monoxide. This invention describes novel methods for the analysis of some of the impurities. The concepts of this invention are not limited to carbon dioxide and are applicable to the analysis of impurities in other gases.

For the purposes of this invention various impurities in carbon dioxide are analyzed by a sulfur analyzer and a hydrocarbon analyzer. Other detectors can be used when analyzing other impurities such as halocarbons in other gases. For carbon dioxide, the two analyzers could be in a single unit such as gas chromatograph or they could be separate units. Prior to analysis, various sulfur and hydrocarbon impurities are concentrated to increase their amounts in the sample. This step improves the detection limits for various analyzers. This is particularly useful for impurities such as benzene which are required to be removed to below 20 ppb for beverage applications. The method involves adsorbing the impurities for several minutes on an adsorbent selective for impurities to be analyzed. For concentrating benzene an adsorbent such as Poropak Q can be used. After adsorbing the impurities the adsorbent column is quickly heated and the impurities are sent to the separation column and then to the detector for quantification. If a gas chromatograph is used for analysis the adsorbent column can be inside the gas chromatograph oven or outside it. To reduce the expenses it is preferable to have the separation column and the adsorption column inside the GC oven.

Concentration of impurities prior to analysis allows use of lower cost detectors for the analysis of various impurities. For instance to measure 20 ppb benzene in the carbon dioxide product an expensive photoionization detector (PID) is needed while after sample concentration a much cheaper flame ionization detector (FID) can be used. Also, for detecting sulfur impurities in the 20 to 50 ppb range an expensive sulfur chemiluminiscence detector (SCD) is needed while after sample concentration a cheaper flame photometric detector (FPD) can be used.

The sulfur analyzer unit will analyze either the total sulfur or individual sulfur species during various process stages. For beverage grade carbon dioxide the total sulfur in the product excluding sulfur dioxide needs to be below 0.1 ppm and sulfur dioxide needs to be below 1 ppm. For the measurement of total sulfur, sulfur impurities are oxidized to sulfur dioxide in a catalytic reactor with a sulfur tolerant catalyst or inside an ozone generator typically based on corona discharge. Sulfur dioxide after the oxidation is analyzed using a sulfur specific detector such as sulfur chemiluminiscence detector (SCD), flame photometric detector (FPD) or pulsed flame photometric detector (PFPD). When speciation of sulfur compounds is required the sulfur impurities may be optionally concentrated and sent directly to a separation column and the detector bypassing the oxidation unit.

The hydrocarbon analyzer will analyze both the total hydrocarbons (as methane) or individual hydrocarbon species in various process stages. For beverage grade carbon dioxide the total hydrocarbons in the product need to be below 50 ppm with different limit for individual components such as benzene (<20 ppb), acetaldehyde (<0.1 ppm) and methanol (<10 ppm). For high purity electronics applications heavy hydrocarbons (>$C_3$) need to be below 0.1 ppm. For the measurement of total hydrocarbons both the sample concentrator and the separation column are bypassed and the sample is sent directly to a FID for measurement. For the measurement of individual hydrocarbon species the sample is sent to a concentrator, and a separation column and sent to a FID detector for analysis.

Details of the analytical system are given in the FIGURE. In the FIGURE, line 14 is the feed line to the analytical skid. Line 16 will direct a portion of the gas sample through valve 18 and line 26 to a multiport valve 28A. A carrier gas such as nitrogen is directed through line 20 and valve 22 to connect with line 26 and mix with the gas sample.

Line 30 directs the gas sample into a concentrator 42A, a separation column 43A and then into a detector 44. The analytical data gathered from this detector is directed along line 48 to a signal to integrator/computer which is not shown. For the analysis of hydrocarbon species a FID (flame ionization detector) can be used.

A further portion of the gas sample is directed along line 14 to line 32 where it is combined with air that enters through line 34. This gas sample is directed to an optional sulfur oxidation catalyst or a ozone generator 36 and through line 38 to a multiport valve 28B. Line 39 directs the sample to a concentrator 42B, a separation column 43B and another detector 46. For the detection of sulfur impurities detector 46 can be a FPD (flame photometric detector). Line 52 exits detector 46 and delivers the analytical data to a signal to integrator/computer, not shown.

The gas chromatography oven 65 will enclose both the detectors such as sulfur and hydrocarbon detection units but can also encompass the concentrator column and the gas chromatography column in one integral unit. This is preferred to reduce the overall analytical system cost.

Valves 28A and 28B in the FIGURE have samples from various locations in the purification process connected to them and the sample location can be controlled with a computer. This allows monitoring of impurities at various stage in the process.

The signals from the detectors are converted to concentration of various impurities through an integrator and/or computer and the information can be displayed for the production operator's use or transmitted to a central location. Should there be a surge of impurities or other data reading indicating that the requisite purity levels are not met, then the operator can pause or stop the purification process while the anomaly is investigated.

The apparatus and processes of the present invention are designed to address concerns with carbon dioxide impurities, particularly with carbon dioxide supplied at the point of use in the manufacturers' process. By purifying and analyzing at the same time, the operator of the production facility can rely on a steady supply of quality assured carbon dioxide.

The industries or customers where the present invention will have utility include but are not limited to the manufacturing and cleaning of foodstuffs; the manufacture of electronics, electronic components and subassemblies; the cleaning of medical products; carbonation of soft drinks, beer and water; blanketing of storage tanks and vessels that contain flammable liquids or powders; blanketing of materials that would degrade in air, such as vegetable oil, spices, and fragrances.

EXAMPLE 1

A sample containing 1 ppm benzene in carbon dioxide at a flow rate of 50 cc/min was passed through different 2.0"×⅛" (5 cm×0.3 cm) columns packed with activated alumina, silica gel, DAY zeolite and Poropak Q, respectively. The column was inside a gas chromatograph oven at 50° C. and connected to a FID detector. The sample flow was continued for about 10 minutes and no benzene breakthrough was seen for any of the columns.

The sample flow was stopped and nitrogen was passed as carrier gas through the column. The column oven was heated to 150° C. in less than one minute and the outlet of the column was monitored using the FID detector. Very little benzene desorption was seen for activated alumina, silica gel and DAY due to their strong affinity for benzene. However, for Poropak Q the entire amount of benzene was desorbed in less than 1 minutes.

For Poropak Q a concentration factor 500 was obtained compared to a 1 cc sample loop. Assuming a benzene detection limit of 0.5 ppm for the FID detector, sample concentration technique allows measurement of benzene concentrations as low as 1 ppb using the same detector. The technique is applicable to other impurities such as aldehydes and alcohols. The technique is also applicable to other gases and other impurities.

The present invention is particularly suited for the analysis of impurities in partially purified product or the final product since lower levels of impurities in the gas streams do not require high adsorption capacity in the concentrators 42A and 42B which operate at ambient or higher temperatures. Also, the adsorbents in these concentrators need to be weak adsorbents (such as Poropak Q for benzene) so that the impurities are easily desorbed as the GC oven is heated. Strong adsorbents such as zeolites and activated alumina may not work well as it will be harder to desorb impurities from them.

While the present invention has been described with reference to several embodiments and example, numerous changes, additions and omissions, as will occur to those skilled in the art, may be made without departing from the spirit and scope of the present invention.

What is claimed is:

1. A method for measuring the concentration of impurities during the purification of a carbon dioxide gas stream comprising:

a) passing a carbon dioxide gas stream containing impurities into a gas adsorption means for a length of time at ambient or higher temperatures to adsorb and remove the impurities therein;
b) stopping the flow of the carbon dioxide gas stream; and
c) desorbing and analyzing the impurities using a detector; wherein the impurities are selected from the group consisting of $H_2S$, dimethyl sulfide and COS.

2. The method of claim 1 wherein the gas adsorption means comprises a packed bed in a gas chromatograph, and wherein the gas chromatograph communicates with an analytical device to measure for sulfur compounds.

3. The method of claim 2 wherein the impurities are desorbed from the packed bed through a gas separation column.

4. The method of claim 1 wherein the detector is selected from a flame ionization detector (FID) and photometric ionization detector (PID) to detect hydrocarbon impurities, and a flame photometric detector (FPD), sulfur chemiluminiscence detector (SCD) and pulsed flame photometric detector (PFPD) to detect sulfur related compounds.

5. The method of claim 3, further comprising increasing a temperature of the gas chromatograph.

6. The method of claim 1 wherein, prior to said passing of the carbon dioxide gas stream containing impurities into the gas adsorption means, sulfur impurities are oxidized to sulfur dioxide in a catalytic reactor with a sulfur tolerant catalyst.

7. The method of claim 1 wherein, prior to said passing of the carbon dioxide gas stream containing impurities into the gas adsorption means, sulfur impurities are oxidized to sulfur dioxide in an ozone generator, optionally by corona discharge.

8. A method for measuring the concentration of impurities during the purification of a carbon dioxide gas stream comprising:
a) passing a carbon dioxide gas stream containing organic compound and sulfur compound impurities into a gas adsorption means for a length of time at ambient or higher temperatures to adsorb and remove the impurities therein;
b) stopping the flow of the carbon dioxide gas stream into the gas adsorption means; and
c) desorbing and analyzing the impurities using a detector; wherein the impurities are selected from the group consisting of sulfur dioxide, $H_2S$, dimethyl sulfide and COS.

9. The method of claim 8 wherein the gas adsorption means comprises a packed bed in a gas chromatograph, and wherein the gas chromatograph communicates with an analytical device to measure for sulfur compounds.

10. The method of claim 9 wherein the impurities are desorbed from the packed bed through a gas separation column, optionally further comprising increasing a temperature of the gas chromatograph.

11. The method of claim 8 wherein the detector is selected from a flame ionization detector (FID) and a photometric ionization detector (PID) to detect the organic compound impurities.

12. The method of claim 8 wherein the detector is selected from a flame photometric detector (FPD), sulfur chemiluminiscence detector (SCD) and a pulsed flame photometric detector (PFPD) to detect the sulfur compound impurities.

13. The method of claim 12 further comprising, prior to said passing of the carbon dioxide gas stream containing impurities into the gas adsorption means, oxidizing the sulfur impurities to sulfur dioxide.

14. The method of claim 13 wherein the sulfur impurities are oxidized in a catalytic reactor with a sulfur tolerant catalyst or inside an ozone generator, optionally by corona discharge.

* * * * *